United States Patent [19]

Alexander et al.

[11] 4,426,391

[45] Jan. 17, 1984

[54] [(ALKOXYCARBONYL)OXY]ALKYL ESTERS OF METHYLDOPA

[75] Inventors: Jose Alexander; Chung Shih, both of Lawrence, Kans.

[73] Assignee: Merck & Co., Inc., Rahway, N.J.

[21] Appl. No.: 418,326

[22] Filed: Sep. 15, 1982

[51] Int. Cl.$^3$ .................. C07C 101/77; A61K 31/265
[52] U.S. Cl. .................................. 424/301; 260/463; 560/40; 562/445
[58] Field of Search ........................ 260/463; 424/301; 560/40, 39

[56] References Cited

U.S. PATENT DOCUMENTS 3,939,270  2/1976  Ekstrom et al. ..................... 424/271
3,983,138  9/1976  Saari ............................... 260/326.43

OTHER PUBLICATIONS

Saari et al., J. Med. Chem., vol. 21, 746–753, (1978).
Saari, Chem. Abs. 83:10873q (1975).
Isaka et al., Chem. Abs. 84:74168s (1976).
Ekstrom et al., Chem. Abs. 87:53266u (1977).

*Primary Examiner*—Donald G. Daus
*Assistant Examiner*—C. Kalita
*Attorney, Agent, or Firm*—Michael C. Sudol, Jr.; Mario A. Monaco

[57] ABSTRACT

Novel prodrugs of methyldopa which are [(alkoxycarbonyl)oxy]alkyl esters of methyldopa are disclosed. Also, pharmaceutical compositions containing these compounds are disclosed. Upon administration to warm-blooded animals, these prodrugs liberate methyldopa along with innocuous side products.

5 Claims, No Drawings

[(ALKOXYCARBONYL)OXY]ALKYL ESTERS OF METHYLDOPA

BACKGROUND AND SUMMARY OF THE INVENTION

The present invention relates to novel and useful prodrugs of methyldopa and the use of these compounds in the treatment of hypertension. More particularly, it relates to [(alkoxycarbonyl)oxy]-alkyl esters of methyldopa useful as prodrugs. The prodrug of my invention on administration to warm blooded animals undergoes enzymatic cleavage to liberate methyldopa along with innocuous side products such as carbon dioxide, $R_3OH$ and $R_1R_2CO$.

Several types of prodrugs of methyldopa are known. For example, U.S. Pat. No. 3,983,138, discloses esters of α-methyl-3,4-dihydroxyphenylalanine different from those of the instant invention. Other prodrugs of methyldopa are also known such as, for example, the POE ester of methyldopa (Journal of Medicinal Chemistry, 1978, Vol. 21, Pages 746–753, "Synthesis and Antihypertensive Activity of Some Ester Progenitors of Methyldopa" By Saari et al.).

Also, bacamapicillin, a Pfizer product, is chemically 1-[(ethoxycarbonyl)oxy]ethyl ester of ampicillin which is an orally administered penicillin. This shows a similar type ester derivative as the instant invention except that the ester of the instant invention is that of methyldopa and not of ampicillin.

It has been suggested in the art that various alanine compounds may be useful in the treatment of hypertension (see U.S. Pat. No. 2,868,818). It is further known in the art that hypertension is preferably treated with L-α-methyl-3,4-dihydroxyphenylalanine since the D-form of the compound is therapeutically inert and only the L-form is therapeutically active. The removal of the D-form thereby lessens toxicity and increases effectiveness (see U.S. Pat. No. 3,344,023 and British Pat. No. 936,074). The L-isomer of L-α-methyl-3,4-dihydroxyphenylalanine is commonly referred to as L-α-methyldopa or methyldopa. It is still further known in the art that the alkyl esters of L- or DL-α-methyl-3,4-dihydroxyphenylalanine are useful in the emergency treatment of hypertension by parenteral administration (see U.S. Pat. No. 3,230,143).

It has now been found that other esters and derivatives of DL- or L-α-methyl-3,4-dihydroxyphenylalanine having specific structures are also active in the treatment of hypertension thereby giving alternative compounds for such treatment.

For compounds which ionize, the rate of transport through biological membranes appears to be proportional to the concentration of undissociated molecules and its degree of lipid solubility. It is often advantageous to perform derivatization of such polar organic compounds to aid absorption. Masking the polar groups will make the compounds more hydrophobic and hence more lipid soluble. The methlyldopa esters of the present invention are synthesized with the objective of obtaining compounds that would be more efficiently absorbed from the gastro intestinal tract than the free amino acid itself and would undergo efficient conversion to methyldopa in the blood or target site. These esters on enzymatic cleavage would release methyldopa and innocuous side products namely, $CO_2$, an aldehyde or ketone $R_1R_2CO$ and an alcohol $R_3OH$. Hence, the carbonate esters of the present invention would not have the undesirable side effects possible with the generation of short chain fatty acids from the very common acyloxyalkyl esters.

Accordingly, it is an object of the present invention to provide a novel and useful class of compounds (prodrugs of methyldopa) which are active in treating hypertension. A further object is to provide a more bioavailable group of compounds for the treatment of hypertension. A still further object is to provide a method of producing such compounds. Another object is to provide a method of treatment for hypertension by the use of the new compounds. Another object is to provide a novel and useful composition for the treatment of hypertension. Other objects will become apparent as the description of the invention proceeds.

These objects are accomplished by the present invention which provides a compound of the formula:

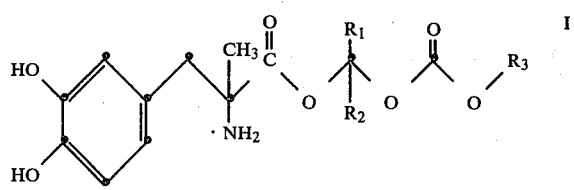

wherein $R_1$ and $R_2$ are independently hydrogen or alkyl having from 1 to 10 carbon atoms (such as methyl, ethyl, pentyl and the like) and $R_3$ is straight or branched chain alkyl having from 1 to 10 carbon atoms, (such as ethyl, isobutyl, t-butyl, isopentyl and the like) and the non-toxic pharmaceutically acceptable acid addition (HX) salts thereof wherein X represents an acid addition salt anion such as chloride, bromide, sulfate, sulfonate, phosphate, nitrate, acetate, propionate, lactate, succinate, tartrate, citrate, ascorbate, maleate, fumarate and the like.

The most preferred compounds of my invention are those compounds of Formula I wherein $R_1$ and $R_2$ are independently H or methyl $R_3$ is straight or branched chain alkyl having from 1–5 carbon atoms and the non-toxic pharmaceutically acceptable acid addition salts thereof.

The present invention further provides an ester of Formula I as defined above of the L-isomer of methyldopa, substantially free of the D-isomer.

With regard to the L-isomer, it should be noted that the assymetric carbon atom is the one containing the amino and methyl group in the acid portion of the molecule. It is this portion of the molecule that is referred to as being in the L-configuration. Note that the L-configuration refers to the stereo configuration and not to the optical rotation, although in this case the L-stereo configuration is the L or levo form of the optical isomer.

The present invention also provides a method of treating hypertension in a hypertensive patient which comprises administering to the patient (both human and animal) a therapeutically effective amount of a compound of formula I as defined above.

In the treatment of hypertension, the compounds of the present invention are generally administered in amounts of from about 0.005 to about 300 mg/kg of body weight of the animal and preferably from about 0.05 to about 100 mg/kg. In a still more preferred embodiment, the compounds are administered in amounts of from about 0.1 to about 25 mg/kg of body weight of the animal. In this regard, it should be noted that the dosage must be adjusted depending upon the activity of the compound, the response desired in the reduction of blood pressure and also the weight of the animal. In the ranges given above, the more active compounds would tend to be given at the lower dosages and the less active compounds at the higher dosages.

The present invention also provides a method of treating hypertension in a hypertensive animal which comprises administering to the animal a therapeutically effective amount of a carbonate ester of the L-isomer of an amino acid, substantially free of the D-isomer, having the formula I.

When the L-isomer of a compound of the present invention is given in the substantial absence of the D-isomer, the required dosage of the L-isomer is approximately one-half of that of the racemate since the D-isomer is therapeutically inactive. However, the compounds of the present invention vary in activity to some degree and thus the racemate of one of the less active compounds of the present invention may require several times the dosage of a more active compound. In general, the compounds will be administered within the above dosages.

The present invention also provides a pharmaceutical composition comprising an inert pharmaceutically acceptable diluent and a compound of the formula I.

In a single dosage form of the composition of the present invention, the active compound is generally present in the composition in amounts of from about 1 mg to about 2,000 mgs, more preferably about 5 mgs to about 1,000 mgs. In a still more preferred embodiment, the active compound is present in amounts of from about 10 mgs to about 500 mgs. The single dosage form of the compound may be administered in a single slow acting dose or it may be administered in several small doses throughout the day, generally 2 to 8 individual dosages.

The present invention also provides a pharmaceutical composition comprising an inert pharmaceutically acceptable diluent and a carbonate ester of the L-isomer of an amino acid, substantially free of the D-isomer, having the formula I.

As in the method of treatment, reduced dosages of the L-isomer substantially free of the D-isomer are required as compared to the racemate. However, the difference in activity of various compounds requires the use of different dosages. In some instances, the compounds are many times more active than others and thus the racemate of one may require even less of a dosage than the L-isomer of a second. In general, however, the dosages will be within the above ranges.

One can prepare the compounds of formula I according to the following equation:

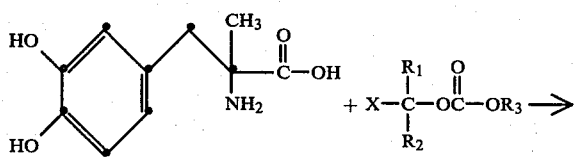

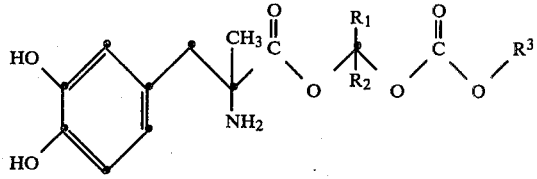

I

Thus, for example, the compounds of formula I can be prepared by treating methyldopa (Formula II) or its O- or N-protected derivatives with [(alkoxycarbonyl-)oxy]alkyl halides of the formula III wherein X is halo such as Cl, I or Br in an appropriate solvent with or without a base followed by deprotection if necessary. Thus, any organic solvent in which the reactants are soluble is suitable for this reaction. This would include: dimethylformamide, dimethylsulfoxide, hexamethylphosphorictriamide, diethyl ether, tetrahydrofuran, dioxane and the like.

Also the reaction is carried out between the temperatures of 0° to 100° and is generally complete in about 16 to 24 hours. The desired products of formula I can be isolated from the reaction mixture by procedures well known in the art such as extraction with an organic solvent, and evaporation of said solvent.

If an O- or N-protected derivative of methyldopa is used, the protecting group can be removed by hydrogenolysis in the presence of an acid for example by dissolving the O- or N-protected ester of methyldopa (I) in a solvent such as acetic acid, adding a catalyst such as palladium on carbon and hydrogenating by adding hydrogen under pressure (to 15 to 60 psi) at a temperature of 0° to 60° but preferably room temperature.

The protection and deprotection part of the reaction described above can also be accomplished by other methods apparent to those who are skilled in the art.

In a preferred embodiment of the present invention, the process above is carried out with the amino acid portion of the molecule of formula I being in the L-stereo configuration.

The pharmaceutically acceptable acid addition salts can be prepared by methods known to those skilled in the art such as by reacting the free amine of Formula I with an equivalent amount of the acid (HX) in a non-aqueous solvent such as ether, chloroform and the like until the salt is formed and then isolating the salt from the reaction mixture, such as by evaporating the solvent, crystallization and the like.

The phrase "the L-isomer of an amino acid", substantially free of the D-isomer, means that the D-isomer is present in amounts not exceeding about 10%. However, it is desireable that the D-isomer be substantially absent from the composition.

The compounds of the present invention can be used in the form of compositions preferably administered in unit dosage form such as tablets, pills, capsules, powders, granules, sterile parenteral solutions or suspensions, oral solutions or suspensions and the like. For preparing solid compositions such as tablets, the principal active ingredient is mixed with conventional tableting ingredients such as corn starch, lactose, sucrose, sorbitol, talc, stearic acid, magnesium stearate, dicalcium phosphate, gums and fractionally similar materials as pharmaceutical diluents or carriers. The tablets or pills of the novel compositions can be laminated or otherwise compounded to provide a dosage from affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The compounds are also useful when administered in the form of suppositories or with a penetrant such as dimethyl sulfoxide.

The liquid forms in which the novel composition of the present invention may be incorporated for administration include suitably flavored emulsions with edible oils, such as, cottonseed oil, sesame oil, coconut oil, peanut and the like, as well as elixirs and similar pharmaceutical vehicles. Suitable dispersing or suspending agents for aqueous suspensions include synthetic and natural gums, such as, tragacanth, acacia, alginate, dextran, sodium carboxymethylcellulose, methylcellulose, polyvinylpyrrolidone, gelatin and the like. Sterile suspensions or solutions are required for parenteral use. Isotonic preparations containing suitable preservatives are also highly desirable for injection use.

The term single dosage form as used in the specification refers to physically discrete units suitable as unitary dosage for warm-blooded animal subjects, each unit containing a predetermined quantity of active material calculated to produce the desired therapeutic effect in association with the required pharmaceutical diluent, carrier or vehicle. The specifications for the novel single dosage forms of this invention are dictated by and are directly dependent on (a) the unique characteristics of the active material and the particular therapeutic effect to be achieved, and (b) the limitations inherent in the art of compounding such an active material for therapeutic use in warm-blooded animals as disclosed in detail in this specification. Examples of suitable oral single dosage forms in accord with this invention are tablets, capsules, pills, powder packets, granules, wafers, cachets, teaspoonfuls, dropperfuls, ampules, vials, segregated multiples of any of the foregoing, and other forms as herein described.

The following examples are given to illustrate the invention and are not intended to limit it in any manner.

EXAMPLE 1

Chloromethyl 3-methyl-1-butyl carbonate

3-Methyl-1-butanol (4.4 g) was dissolved in dichloromethane (75 ml) and pyridine (4.0 g) was added to it. The reaction mixture was cooled in an ice bath and chloromethyl chloroformate (6.5 g) was added to it with stirring. The cooling bath was removed and the reaction mixture was stirred at room temperature for 16 hours. The dichloromethane solution was washed with water thrice and once with brine. The organic layer was dried over sodium sulfate and evaporated to furnish a colorless oil of desired product weighing 10.7 g which was the pure chloromethyl isopentyl carbonate. NMR (CDCl$_3$) δ 0.95 (6H, d, J=5 Hz, CH(C$\underline{H}_3$)$_2$), 1.66 (3H, m, C$\underline{H}_2$ and C$\underline{H}$), 4.28 (2H, t, J=7 Hz, OC$\underline{H}_2$CH$_2$) and 5.73 (2H, s, OC$\underline{H}_2$Cl). IR (film) 2950, 1783, 1265 cm$^{-1}$.

1-Chloroethyl ethyl carbonate

Ethanol (2.3 g) was dissolved in dichloromethane (50 ml) and pyridine (4.0 g) was added. It was reacted with 1-chloroethyl chloroformate (7.5 g) as described above. On work up it gave 7.5 g of a pale mobile liquid (desired product). NMR (CDCl$_3$) δ1.36 (3H, t, J=7 Hz, OCH$_2$C$\underline{H}_3$), 1.88 (3H, $\underline{d}$, J=7 Hz, ClCH$_2$CH$_3$), 4.36 (2H, q, J=7 Hz, OC$\underline{H}_2$CH$_3$) and 6.41 (1H, q, J=7 Hz, CH$_3$C$\underline{H}$Cl).

Chloromethyl chloroformate and chloroethyl chloroformate can be reacted similarly with other alcohols such as t-butanol and hexanol to form 1-chloromethyl (or ethyl) t-butyl carbonate and 1-chloromethyl (or ethyl) +-butyl carbonate and 1-chloromethyl (or ethyl) hexyl carbonate.

EXAMPLE 2

Iodomethyl 3-methyl-1-butyl carbonate

Chloromethyl isopentyl carbonate (4.2 g) was dissolved in dry acetone (25 ml) and anhydrous sodium iodide (6.0 g) was added to it. The reaction mixture was stirred at room temperature protected from light for 6 hours. The acetone was evaporated off. The residue was taken in water (50 ml) and extracted with ether. The ether extract was washed successively with aqueous sodium bisulfite, water and brine and dried over sodium sulfate. Evaporation of ether gave a light-yellow oil of product weighing 6.1 g NMR (CDCl$_3$)δ 0.96 (6H, d, J=5 Hz, (C$\underline{H}_3$)$_2$), 1.63 (3H, m, C$\underline{H}_2$C$\underline{H}$), 4.26 (2H, t, J=7 Hz, OC$\underline{H}_2$) and 5.96 (2H, s, C$\underline{H}_2$I).

Other chloromethyl and chloroethyl carbonates as shown in Example 1 can be converted to their corresponding iodo derivatives following the same procedure except for iodomethyl t-butyl carbonate which is unstable.

EXAMPLE 3

[(3-Methyl-1-butyloxy carbonyl)oxy]methyl N-benzyloxy carbonyl-[3,4-dibenzyloxycarbonyloxy)-phenyl]-2-methyl alanine ester To a solution of 12.0 g of N-benzyloxycarbonyl-[3,4-di-(benzyloxycarbonyloxy)-phenyl]-2-methyl alanine in ether (25 ml) and hexamethylphosphoric triamide (25 ml), 2.1 g of triethylamine was added with stirring. To this solution 6.0 g of iodomethyl 3-methyl-1-butyl carbonate was added. The reaction mixture was kept stirred at room temperature for 24 hours. It was then diluted with 175 ml of water and the ether layer was separated. The aqueous layer was extracted with ether. The combined ether extract was washed successively with water, aqueous sodium bisulfite, aqueous sodium bicarbonate and water. The ether extract was then dried over sodium sulfate and evaporated to a thick oil weighing 14.6 g. It was purified by chromatography over silica gel (150 g). Elution with dichloromethane containing 10% v/v of ethyl acetate and evaporation of the solvent furnished 12.1 g of the pure carbonate ester as a colorless thick oil. NMR (CDCl$_3$)δ 0.87 (6H, d, J=5 Hz, CH(C$\underline{H}_3$)$_2$), 1.53 (3H, s, C$\underline{H}_3$C), 1.16 (3H, m, C$\underline{H}_2$CH(CH$_3$)$_2$), 3.25 (2H, s Ar C$\underline{H}_2$), 4.23 (2H, t, J=6

Hz, OCH₂CH₂), 5.1 (2H, s, NHCOOCH₂), 5.18 (4H, s, OCOOCH₂), 5.76 (2H, s, OCH₂O), 6.7–7.5 (18H, m, aromatic). IR (film) 3396, 1780 shoulder, 1765, 1738, 1514, 1260, 1200 cm⁻¹.

Other carbonate esters of 0,0', N-protected methyldopa are prepared by reacting said protected methyldopa compound with the corresponding iodo compound. In the case of a t-butyl derivative, chloromethyl t-butyl carbonate rather than iodomethyl t-butyl carbonate was used in the experiment because of the instability of said corresponding iodo compound.

EXAMPLE 4

[(3-Methyl-1-butyloxycarbonyl)oxy]methyl (3,4-dihydroxyphenyl)-2-methylalanine ester acetate salt The above tri-protected methyldopa carbonate ester (12 g) was dissolved in acetic acid (100 ml) and 3 g of 10% Pd on charcoal was added as a suspension in glacial acetic acid (10 ml). It was hydrogenated at 50 psi at room temperature. Hydrogenolysis was complete in 4 hours. The catalyst was filtered off and the acetic acid was evaporated. The residue was vacuum dried to a thick glue weighing 4.64 g. It was then triturated with ether and filtered. The filtrate was evaporated to a foam weighing 2.1 g. NMR (CDCl₃)δ 0.95 (6H, d, J=6 Hz, CH(CH₃)₂), 1.48 (3H, s, CH₃C), 1.53 (3H, m, CH₂CH), 2.91 (2H, broad q, ArCH₂), 4.21 (2H, t, OCH₂CH₂), 5.75 (2H, s, OCH₂O), 6.35–6.95 (3H, m, aromatic), 7.33 (broad NH₃+) and 1.98 (3H, s, CH₃COO⁻).

Other carbonate ester derivatives can be deprotected similarly by hydrogenolysis with pd—C in a suitable solvent in the presence of an acid.

Many other equivalent modifications will be apparent to those skilled in the art from a reading of the foregoing without a departure from the inventive concept.

What is claimed is:

1. A compound of the formula:

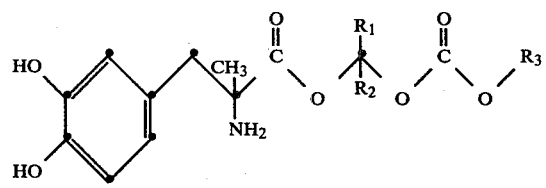

wherein
R₁ and R₂ are independently hydrogen or alkyl having from 1 to 10 carbon atoms;
R₃ is alkyl having from 1–10 carbon atoms
or a non-toxic pharmaceutically acceptable acid addition salt thereof.

2. A compound of the formula:

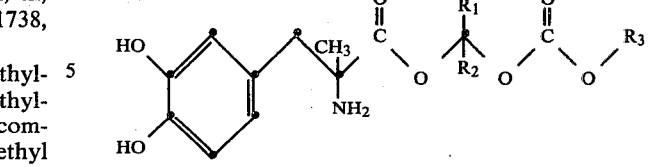

wherein
R₁ and R₂ are independently hydrogen or methyl
R₃ is alkyl having from 1 to 5 carbon atoms
or a non-toxic pharmaceutically acceptable acid addition salt thereof.

3. A compound of claim 1 which is [(3-Methyl-1-butyloxycarbonyl)oxy]methyl (3,4-dihydroxyphenyl)-2-methylalanine ester acetate salt.

4. A method of treating hypertension which comprises administering to a patient in need of such treatment a pharmaceutically effective amount of a compound of the formula:

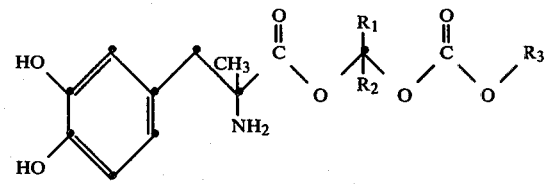

wherein
R₁ and R₂ are independently hydrogen or alkyl having up to 10 carbon atoms;
R₃ is alkyl having 1 to 10 carbon atoms
or a pharmaceutically acceptable non-toxic acid addition salt thereof.

5. An antihypertensive pharmaceutical composition comprising an effective amount of a compound of the formula:

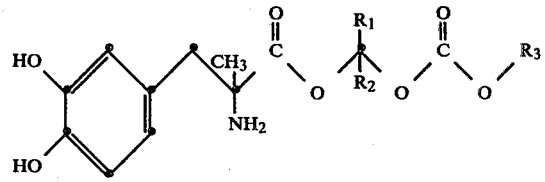

wherein
R₁ and R₂ are independently hydrogen or alkyl having up to 10 carbon atoms;
R₃ is alkyl having from 1 to 10 carbon atoms
or a non-toxic pharmaceutically acceptable acid addition salt thereof.

* * * * *